United States Patent [19]

Nowicki et al.

[11] Patent Number: 4,769,488

[45] Date of Patent: Sep. 6, 1988

[54] BATCH OR SEMICONTINUOUS PSEUDOCUMENE OXIDATION AND CATALYST RECOVERY AND RECYCLE

[75] Inventors: Neal R. Nowicki, Naperville; Donald E. Thomka, Romeoville, both of Ill.

[73] Assignee: Amoco Corporation, Chicago, Ill.

[21] Appl. No.: 790,379

[22] Filed: Oct. 23, 1985

Related U.S. Application Data

[63] Continuation-in-part of Ser. No. 565,915, Dec. 27, 1983, abandoned.

[51] Int. Cl.⁴ ............................................. C07C 51/265
[52] U.S. Cl. ..................................................... 562/414
[58] Field of Search ......................................... 562/414

[56] References Cited

U.S. PATENT DOCUMENTS 4,488,999 12/1984 Feld ................................ 562/414 X
4,587,355 5/1986 Brown et al. ........................ 562/414

Primary Examiner—Michael L. Shippen
Attorney, Agent, or Firm—Gunar J. Blumberg; William H. Magidson; Ralph C. Medhurst

[57] ABSTRACT

A method is disclosed for the liquid-phase oxidation of pseudocumene in the presence of an oxidation catalyst comprising cobalt, manganese, and bromine components wherein the metal catalyst are recycled to the oxidation reactor in the form of their oxalates.

8 Claims, No Drawings

BATCH OR SEMICONTINUOUS PSEUDOCUMENE OXIDATION AND CATALYST RECOVERY AND RECYCLE

BACKGROUND

This application is a continuation-in-part application of Serial No. 565,915 filed on Dec. 27, 1983, now abandoned.

The field of this invention relates to the recovery of the cobalt from the catalyst used in liquid-phase oxidation of pseudocumene to trimellitic acid.

SUMMARY OF THE INVENTION

Our novel process relates to the recovery of trimellitic anhydride (TMA) catalyst by high temperature oxalate precipitation and separation followed by recycle of the recovered oxalates to the oxidation reactor.

Because of the high cobalt consumption in the TMA process, a catalyst recovery is very advantageous. Aqueous extraction from residue does not work for TMA because the residue is too soluble in water and because the metals are complexed with aromatic acids.

DETAILED DESCRIPTION OF THE INVENTION

Our application Ser. No. 565,915 filed Dec. 27, 1983, now abandoned, described a novel catalyst recovery process for the continuous oxidation of pseudocumene. The high level of catalyst used in this process required such a recovery process in order to be economical. Even in batch oxidations as commercially practiced and in semi-continuous oxidations, the recovery of the catalyst metals is highly desirable. Our novel process is particularly applicable to batch and semi-continuous pseudocumene oxidation processes.

The effluent leaving the reactor contains trimellitic acid (TMLA), acetic acid, and the catalyst metals. As commercially practiced, most of the TMLA is soluble in the solvent as it exits the reactor. The addition of oxalic acid to this stream gives a precipitate which is suitably recovered by filtration or centrifugation. This precipitate is advantageously used to replace part or all of the cobalt in the oxidation catalyst thus effecting a great economy in the manufacture of TMLA and TMA. Other catalyst components are suitably added to effect the optimum catalyst composition. A unique feature of our novel process is that manganese and zirconium are not quantitatively recovered. Most of these components are added later in the oxidation. The same is true for bromine; its recovery is low, allowing a steady addition of bromine to the oxidation during the whole oxidation process. Furthermore, recovery of sodium is low which prevents undesirable side effects in the oxidation. Some sodium is present to reduce corrosion in the dehydration towers.

Advantageously, the reclaimed catalyst is subjected to a heat treatment at 400°–500° F. in acetic acid prior to recycle to the oxidation to improve the activity and selectivity of the catalyst.

Suitable solvents for use in the process for the oxidation of pseudocumene to TMLA include any $C_2$–$C_6$ fatty acids such as acetic acid, propionic acid, n-butyric acid, isobutyric acid, n-valeric acid, trimethylacetic acid, caproic acid, and water and mixtures thereof. Preferably, the solvent is a mixture of acetic acid and water, which more preferably contains from 1 to 20 weight percent of water, as introduced into the oxidation reactor. The weight ratio of the solvent to pseudocumene introduced into the reactor in the liquid-phase oxidation of this invention is in the range of from about 19:1 to about 3:1, and preferably from about 6:1 to about 4:1.

The source of molecular oxygen for the oxidation of this invention can vary in molecular oxygen content from that of air to oxygen gas. Air is the preferred source of molecular oxygen. In order to avoid the formation of explosive mixtures, the oxygen-containing gas fed into the reactor should provide an exhaust gas-vapor mixture containing from 2 to 8 volume percent oxygen (measured on a solvent-free basis). For example, when each alkyl substituent on the aromatic ring of the alkyl aromatic is a methyl group, a feed rate of the oxygen-containing gas sufficient to provide oxygen in the amount of from 1.6 to 2.8 moles per methyl group will provide such 2 to 8 volume percent of oxygen (measured on a solvent-free basis) in the gas-vapor mixture in the condenser.

The catalyst employed in the method of this invention comprises cobalt, manganese, and bromine components. The weight ratio of cobalt (calculated as elemental cobalt) in the cobalt component of the catalyst to the alkyl aromatic in the liquid-phase oxidation of the method of this invention is in the range of from about 0.5 to about 10 milligram atoms (mga) per gram mole of the alkyl aromatic. The weight ratio of manganese (calculated as elemental manganese) in the manganese component of the catalyst to cobalt (calculated as elemental cobalt) in the cobalt component of the catalyst in the liquid-phase oxidation of the method of this invention is in the range of from about 0.2 to about 10 mga per mga of cobalt. The weight ratio of bromine (calculated as elemental bromine) in the bromine component of the catalyst-to-total cobalt manganese (calculated as elemental cobalt and elemental manganese) in the cobalt and manganese components of the catalyst in the liquid-phase oxidation of the method of this invention is in the range of from about 0.2 to about 1.5 mga per mga of total cobalt and manganese.

In the event that soluble forms of the cobalt components are introduced into the liquid-phase oxidation of this invention, each of the cobalt components can be provided in any of its known ionic or combined forms that are soluble in the solvent. For example, when the solvent is an acetic acid medium, cobalt carbonate, acetate tetrahydrate, and/or bromide can be employed. The 0.2 to 1.5:1.0 elemental bromine-to-total cobalt and manganese milligram atom ratio is provided by a source of bromine. Such bromine sources include elemental bromine ($Br_2$), ionic bromide (for example $NH_4Br$, NaBr, KBr, etc.), or organic bromides which are known to provide bromide ions at the operating temperature of the oxidation (e.g., bromobenzenes, benzylbromide, mono- and di-bromoacetic acid, bromoacetyl bromide, tetrabromethane, ethylene-dibromide, etc.). The total bromine in molecular bromine and ionic bromide is used to determine satisfaction of the elemental bromine-to-total cobalt and manganese milligram atom ratio of 0.2-1.5:1.0. The bromide ion released from the organic bromides at the oxidation operating conditions can be readily determined by known analytical means. Tetrabromethane, for example, at operating temperatures such as 170° to 225° C. has been found to yield about 3 effective gram atoms of bromine per gram mole.

In operation, the minimum pressure at which the reactor is maintained is that pressure which will maintain a substantial liquid phase of the pseudocumene and at least 70 percent of the solvent. The alkyl aromatic and solvent not in the liquid phase because of vaporization is removed from the reactor as a vapor-gas mixture, condensed, and then returned to the reactor in the recycle solvent. When the solvent is an acetic acid-water mixture, suitable reaction gauge pressures are in the range of from about 0 kg/cm$^2$ to about 35 kg/cm$^2$, and typically are in the range of from about 10 kg/cm$^2$ to about 30 kg/cm$^2$.

The temperature range within the reactor is generally from about 120° C. to about 240° C., and preferably from about 150° C. to about 230° C.

In a preferred embodiment of the method of this invention, the recovered cobalt oxalate introduced into the liquid-phase oxidation obtained by introducing either solid oxalic acid or a solid metal oxalate or an aqueous solution of either thereof into at least a portion of the product stream withdrawn from the oxidation reactor to precipitate cobalt ions therein as cobalt oxalate and then separating the cobalt oxalate precipitates and recycling them to the liquid-phase oxidation. In the preferred embodiment, the oxalic acid to metals molar ratio is 0.25 to 2.5, most preferably 0.5 to and separated from 1.5. As shown in U.S. Ser. No. 565,915, these molar ratios lead to high cobalt recovery. Cobalt is the most expensive component of our catalyst package. Addition of greater than 1.5 moles of oxalic acid does not substantially increase cobalt recovery. Metal oxalates suitable for introduction into the product stream include sodium oxalate, potassium oxalate, lithium oxalate, cesium oxalate, and ammonium oxalate.

In the preferred embodiment, oxalic acid or the metal oxalate is added to the oxidation reactor effluent at temperatures of about 250° F. to about 375° F. prior to separation of the product trimellitic acid. As shown in Example 1, greater than 95% cobalt recoveries can be demonstrated at 305° F. using 1.22 moles of oxalic acid per mole of total catalyst metals. Cobalt is the most expensive catalyst component. In our recovery process the oxalate salts form rapidly, even from cobalt and manganese previously tied up as insoluble trimellitate salts. The oxalates are readily recovered from the acetic acid solvent, in which they are insoluble, by high temperature separation, by high pressure centrifugation, or by hydroclones. The solid oxalate product can be directly recycled to the reactor or more preferably be subjected to heat treatment in water at about 400° F. to about 500° F.

It is particularly advantageous to run the precipitation step at a temperature of about 275° F. to about 325° F. so that a very high percentage of the product TMLA remains dissolved in the mother liquor and is readily separated from the catalyst precipitate. Temperatures in excess of about 375° F. cannot be used in our recovery process, since the oxalate salts of cobalt and manganese decompose. As a result, the recovery of these metals decreases.

In our commercial applications we believe that the removal of the metals prior to product recovery is beneficial. The presence of the metals in the crude TMLA can affect subsequent dehydration to the desired anhydride product and further downstream processing.

Stoichiometrically, one mole of oxalic acid and/or the oxalate ion can react with one gram atom of each of the cobalt or manganese ion to form the corresponding hydrated salt. However, since the extent of this reaction is influenced by the concentration of the reactants, the pH and temperature of the medium, the presence of oxygen and other factors, the number of moles of oxalic acid and/or oxalate ion to be added per gram atom of total cobalt and manganese content falls in the range of about 0.25 to about 2.5 moles of oxalic acid per gram atom of total metals catalysts.

The following example will serve to provide a full understanding of the invention, but it is to be understood that these examples are given for illustrative purposes only and will not be interpreted as limiting the invention in any way.

EXAMPLE 1

The catalyst recovery process was carried out as follows. 439 grams of a slurry whose composition is set forth in Table 1 were charged into a one liter titanium clad autoclave reactor. The reactor was heated to 300° F. under nitrogen and maintained for approximately 10 minutes. Oxalic acid at a 1.22 mole ratio was added as a dilute aqueous solution using a Ruska pump. After approximately 5 minutes, a valve at the bottom of the reactor was opened to start the filtration. Some plugging of the one micron titanium filter was observed, however, the plug was removed by increasing the reactor pressure. Filtration was complete in approximately 10 minutes.

Table 1 summarizes the results of the run. As can be seen from this data, greater than 98% of the cobalt and 47% of the manganese were recovered employing our novel process. By adding the oxalic acid as a dilute solution, the solvent ratio has been significantly increased, from 3.2:1 to 3.9:1. The result is that nearly all of the TMLA is soluble at the 300° F. separation temperature. Out of 439 grams of slurry (31.0 by weight solids) only 3.64 grams of solids were recovered on the filter. The oxalate salts of cobalt and manganese recovered can account for 68% of this weight. The remainder is TMLA.

TABLE 1

| Catalyst Recovery in Trimellitic Acid Slurry by Oxalate Precipitation at 305° F.[a] | | |
|---|---|---|
| Starting Material (g) | | |
| Sample Weight | 439 | |
| Solids | 136 | |
| % TS (Total Solids) | 31.0 | |
| Catalyst | | |
| Co | 0.714 | |
| Mn | 0.162 | |
| Br | 1.707 | |
| Oxalic Acid | 2.3[b] | |
| | Run Number 6090-184 | |
| Sample (g) | Reactor | Filtrate |
| Sample Weight | 3.64 | 502 |
| Dried Solids | — | 109.9 |
| % TS | — | 21.9% |
| Catalyst | | |
| Co | 0.728 | 0.012 |
| Mn | 0.069 | 0.076 |
| Br | 0.006 | 1.518 |
| Catalyst Recovery (%) | | |
| Co | 98.4 | |
| Mn | 47.6 | |
| Accountability | Wt (g) | % Accountability |
| Total Sample | 505.6 | 95.8 |
| Solids | 111.2 | 81.8 |
| Catalyst | | |
| Co | 0.740 | 103.6 |

TABLE 1-continued

Catalyst Recovery in Trimellitic Acid
Slurry by Oxalate Precipitation at 305° F.[a]

| | | |
|---|---|---|
| Mn | 0.145 | 89.5 |
| Br | 1.524 | 89.3 |

[a]Runs made using continuous feed material in a one-liter titanium clad autoclave.
[b]Oxalic acid dihydrate added as a 2.6% by weight aqueous solution.

We claim:

1. A process for producing trimellitic acid by the liquid-phase oxidation of pseudocumene in a batch process with an oxygen-containing gas in a solvent at an elevated temperature and pressure and in the presence of an oxidation catalyst comprising cobalt, manganese, and bromine components to produce an oxidation reactor effluent wherein weight ratio of said solvent to said pseudocumene is in the range of from about 19:1 to about 3:1 at a minimum reactor pressure which maintains a substantial liquid phase of said pseudocumene and at least 70 percent of said solvent, and said solvent is selected from the group consisting of any $C_2$–$C_6$ fatty acid and water, and mixtures thereof, the improvement in combination therewith comprising at least a portion of the cobalt and manganese catalyst components initially contacted with the pseudocumene and oxygen-containing gas is in the form of recovered oxalate salts of cobalt and manganese and wherein these salts have been obtained from the addition of solid oxalic acid, metal oxalates, or solutions thereof to said reactor effluent and recovering these salts by high temperature physical separation conducted at a temperature of about 250° F. to about 375° F. prior to separating trimellitic acid product cake from mother liquor.

2. The process of claim 1 wherein the high temperature physical separation is conducted by filtration.

3. The process of claim 1 wherein the high temperature separation is conducted in a hydroclone.

4. The process of claim 1 wherein the solvent is an acetic acid medium.

5. The process of claim 1 wherein the temperature of said reactor effluent, is in the range of from about 275° F. to about 325° F., prior to separation of the product trimellitic acid.

6. The process of claim 1 wherein the oxygen-containing gas is air.

7. The process of claim 1 wherein the cobalt component, calculated as elemental cobalt, is present at a level of 0.5 to 10 milligram atoms per gram mole of pseudocumene, the manganese component, calculated as elemental manganese, is present at a level of 0.2 to 10 milligram atoms per milligram atom of cobalt, and the bromine component, calculated as elemental bromine, is present at a level of 0.2 to 1.5 gram atoms per gram atom of total cobalt and manganese.

8. The process of claim 1 wherein said pseudocumene is added as a continuous feed.

* * * * *

UNITED STATES PATENT OFFICE
CERTIFICATE OF CORRECTION

Patent No. 4,769,488          Dated September 6, 1988

Inventor(s) Neal R. Nowicki, Donald E. Thomka

It is certified that error appears in the above-identified patent and that said Letters Patent are hereby corrected as shown below:

| Column | Line | |
|---|---|---|
| 3 | 26-27 | Reads "0.5 to and separated from 1.5." and should read --0.5 to 1.5-- |
| 3 | 36 | Reads "added to the" and should read --added to and separated from the-- |

Signed and Sealed this

Fourth Day of April, 1989

Attest:

DONALD J. QUIGG

Attesting Officer

Commissioner of Patents and Trademarks